(12) United States Patent
Collins et al.

(10) Patent No.: US 8,075,312 B2
(45) Date of Patent: Dec. 13, 2011

(54) DENTAL IMPLANT WITH IMPROVED OSSEOINTEGRATION FEATURES

(75) Inventors: Michael Collins, San Marcos, CA (US); Jeffrey A. Bassett, Vista, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 0 days.

(21) Appl. No.: 12/065,259

(22) PCT Filed: Aug. 30, 2006

(86) PCT No.: PCT/US2006/033893
§ 371 (c)(1),
(2), (4) Date: Jun. 4, 2008

(87) PCT Pub. No.: WO2007/027794
PCT Pub. Date: Mar. 8, 2007

(65) Prior Publication Data
US 2008/0241793 A1    Oct. 2, 2008

Related U.S. Application Data

(60) Provisional application No. 60/712,577, filed on Aug. 30, 2005.

(51) Int. Cl.
*A61C 8/00* (2006.01)
(52) U.S. Cl. ...................................................... 433/173
(58) Field of Classification Search ................... 433/173, 433/174
See application file for complete search history.

(56) References Cited

U.S. PATENT DOCUMENTS

| | | | |
|---|---|---|---|
| 2,721,387 A | 10/1955 | Ashuckian | |
| 3,314,420 A | 4/1967 | Smith et al. | |
| 3,423,830 A | 1/1969 | Halpern et al. | |
| 3,423,831 A | 1/1969 | Semmelman | |
| 3,497,953 A * | 3/1970 | Weissman | 433/173 |
| 3,685,115 A | 8/1972 | Scott | |
| 3,713,860 A | 1/1973 | Auskern | |

(Continued)

FOREIGN PATENT DOCUMENTS
CA    2506845    7/2004
(Continued)

OTHER PUBLICATIONS

An Introduction to Silanes and Their Clinical Applications in Dentistry, Jukka P.I Matinlinna et al., vol. 17, No. 2, pp. 155-164 The International Journal of Prosthodontics, 2004.

(Continued)

*Primary Examiner* — Ralph Lewis
(74) *Attorney, Agent, or Firm* — Miller, Matthias & Hull LLP (57) ABSTRACT

Dental implants made at least in part of a highly porous biomaterial such as porous tantalum for enhancing the osseointegration of the dental implant into surrounding bone. For example, there is provided a dental implant which includes a core formed of with a head portion having an abutment interface and a stem portion extending from the head portion. A porous tantalum sleeve is disposed about the stem portion and occupies a substantial portion of the implant/bone interface of the implant. After implantation of the implant, bone tissue may osseointegrate into the porous tantalum sleeve to anchor the implant in position within the surrounding bone. Other embodiments of implants are provided, each implant including at least a portion thereof formed of porous tantalum for improved osseointegration.

4 Claims, 9 Drawing Sheets

U.S. PATENT DOCUMENTS

| | | |
|---|---|---|
| 3,740,851 A | 6/1973 | Weissman |
| 3,797,113 A | 3/1974 | Brainin |
| 3,849,887 A | 11/1974 | Brainin |
| 3,896,547 A | 7/1975 | Kulwiec |
| 3,905,109 A | 9/1975 | Cohen et al. |
| 3,906,550 A | 9/1975 | Rostoker |
| 3,919,773 A | 11/1975 | Freeman |
| 3,934,347 A | 1/1976 | Lash et al. |
| 3,992,725 A | 11/1976 | Homsy |
| 4,011,602 A * | 3/1977 | Rybicki et al. ............. 623/23.76 |
| 4,016,651 A | 4/1977 | Kawahara et al. |
| 4,086,701 A | 5/1978 | Kawahara et al. |
| 4,097,935 A | 7/1978 | Jarcho |
| 4,122,605 A | 10/1978 | Hirabayashi et al. |
| 4,131,597 A | 12/1978 | Bluethgen |
| 4,178,686 A | 12/1979 | Riess et al. |
| 4,195,366 A | 4/1980 | Jarcho et al. |
| 4,199,864 A | 4/1980 | Ashman |
| 4,229,170 A | 10/1980 | Perez |
| 4,244,689 A | 1/1981 | Ashman |
| 4,252,525 A | 2/1981 | Child |
| 4,259,072 A | 3/1981 | Hirabayashi et al. |
| 4,281,991 A | 8/1981 | Michi et al. |
| 4,321,042 A | 3/1982 | Scheicher |
| 4,375,967 A | 3/1983 | Schaeffer |
| 4,379,694 A | 4/1983 | Riess |
| 4,381,918 A | 5/1983 | Ehmford |
| 4,411,624 A | 10/1983 | Ogino et al. |
| 4,431,420 A | 2/1984 | Adair |
| 4,439,152 A * | 3/1984 | Small ........................... 433/173 |
| 4,448,758 A | 5/1984 | Nagai et al. |
| 4,475,892 A | 10/1984 | Faunce |
| 4,478,904 A | 10/1984 | Ducheyne et al. |
| 4,483,678 A | 11/1984 | Nishio et al. |
| 4,492,577 A | 1/1985 | Farris et al. |
| 4,531,915 A | 7/1985 | Tatum, Jr. |
| 4,531,916 A | 7/1985 | Scantlebury et al. |
| 4,536,158 A | 8/1985 | Bruins et al. |
| 4,548,959 A | 10/1985 | Nagai et al. |
| 4,556,534 A | 12/1985 | Burnett |
| 4,708,652 A | 11/1987 | Fujiu et al. |
| 4,713,006 A | 12/1987 | Hakamatsuka et al. |
| 4,722,688 A | 2/1988 | Lonca |
| 4,731,085 A | 3/1988 | Koch |
| 4,737,411 A | 4/1988 | Graves, Jr. et al. |
| 4,743,260 A | 5/1988 | Burton |
| 4,744,757 A | 5/1988 | Adair et al. |
| 4,744,759 A | 5/1988 | Bowen |
| 4,820,157 A | 4/1989 | Salvo |
| 4,842,517 A | 6/1989 | Kawahara et al. |
| 4,871,384 A | 10/1989 | Kasuga |
| 4,872,839 A | 10/1989 | Brajnovic |
| 4,872,840 A | 10/1989 | Bori |
| 4,877,400 A | 10/1989 | Holsclaw |
| 4,880,610 A | 11/1989 | Constantz |
| 4,906,190 A | 3/1990 | Michna |
| 4,909,738 A | 3/1990 | Ai et al. |
| 4,957,554 A | 9/1990 | Mathers et al. |
| 4,957,819 A * | 9/1990 | Kawahara et al. ............ 428/547 |
| 4,960,733 A | 10/1990 | Kasuga et al. |
| 4,969,817 A | 11/1990 | Hiranuma et al. |
| 4,969,913 A | 11/1990 | Ojima |
| 4,983,182 A | 1/1991 | Kijima et al. |
| 5,000,685 A | 3/1991 | Brajnovic |
| 5,002,488 A | 3/1991 | Homsy |
| 5,004,421 A | 4/1991 | Lazarof |
| 5,007,835 A | 4/1991 | Valen |
| 5,009,709 A | 4/1991 | Ibsen et al. |
| 5,049,074 A * | 9/1991 | Otani et al. ................... 433/173 |
| 5,055,497 A | 10/1991 | Okada et al. |
| 5,061,285 A | 10/1991 | Koch |
| 5,062,798 A | 11/1991 | Tsuge et al. |
| 5,064,731 A | 11/1991 | Miyazaki et al. |
| 5,076,789 A | 12/1991 | Tanaka |
| 5,087,200 A | 2/1992 | Brajnovic et al. |
| 5,120,340 A | 6/1992 | Ducheyne et al. |
| 5,123,844 A | 6/1992 | Wakai et al. |
| 5,125,839 A | 6/1992 | Ingber et al. |
| 5,125,971 A | 6/1992 | Nonami et al. |
| 5,139,424 A | 8/1992 | Yli-Urpo |
| 5,152,687 A | 10/1992 | Amino |
| 5,176,747 A | 1/1993 | Panzera et al. |
| 5,180,303 A | 1/1993 | Hornburg et al. |
| 5,186,626 A | 2/1993 | Tanaka |
| 5,192,325 A | 3/1993 | Kijima et al. |
| 5,194,000 A | 3/1993 | Dury |
| 5,194,001 A | 3/1993 | Salvo |
| 5,199,873 A | 4/1993 | Schulte et al. |
| 5,205,745 A | 4/1993 | Kamiya et al. |
| 5,232,365 A | 8/1993 | Ikehara |
| 5,232,878 A | 8/1993 | Kasuga et al. |
| 5,236,458 A | 8/1993 | Ducheyne et al. |
| 5,238,405 A | 8/1993 | Marlin |
| 5,254,005 A | 10/1993 | Zuest |
| 5,282,861 A * | 2/1994 | Kaplan ...................... 623/23.51 |
| 5,282,863 A | 2/1994 | Burton |
| 5,288,232 A | 2/1994 | Panzera et al. |
| 5,306,673 A | 4/1994 | Hermansson et al. |
| 5,308,391 A | 5/1994 | Komma et al. |
| 5,310,343 A | 5/1994 | Hasegawa et al. |
| 5,312,254 A | 5/1994 | Rosenlicht |
| 5,314,334 A | 5/1994 | Panzera et al. |
| 5,342,201 A | 8/1994 | Oden |
| 5,344,318 A | 9/1994 | Wilson et al. |
| 5,344,457 A | 9/1994 | Pilliar et al. |
| 5,346,397 A | 9/1994 | Braiman |
| 5,415,546 A | 5/1995 | Cox, Sr. |
| 5,419,702 A | 5/1995 | Beaty et al. |
| 5,425,640 A | 6/1995 | Scharf |
| 5,439,380 A | 8/1995 | Marlin |
| 5,443,515 A | 8/1995 | Cohen et al. |
| 5,458,488 A * | 10/1995 | Chalifoux ..................... 433/173 |
| 5,468,544 A | 11/1995 | Marcolongo et al. |
| 5,476,383 A | 12/1995 | Beaty et al. |
| 5,549,123 A | 8/1996 | Okuyama et al. |
| 5,554,665 A | 9/1996 | Tateosian et al. |
| 5,562,733 A | 10/1996 | Weissbach et al. |
| 5,571,016 A | 11/1996 | Ingber et al. |
| 5,572,652 A | 11/1996 | Robusto et al. |
| 5,575,652 A | 11/1996 | Gaffar et al. |
| 5,584,693 A | 12/1996 | Nishihara |
| 5,591,030 A | 1/1997 | Thiel et al. |
| 5,612,049 A | 3/1997 | Li et al. |
| 5,614,330 A | 3/1997 | Panzera et al. |
| 5,621,035 A | 4/1997 | Lyles et al. |
| 5,624,262 A | 4/1997 | Yarovesky et al. |
| 5,645,934 A | 7/1997 | Marcolongo et al. |
| 5,674,069 A | 10/1997 | Osorio |
| 5,676,745 A | 10/1997 | Kelly et al. |
| 5,683,249 A | 11/1997 | Ibesen et al. |
| 5,685,714 A | 11/1997 | Beaty et al. |
| 5,695,337 A | 12/1997 | Tyszbiat Sadoun |
| 5,697,785 A | 12/1997 | Delahaye |
| 5,697,976 A | 12/1997 | Chesterfield et al. |
| 5,697,997 A | 12/1997 | Aronsson et al. |
| 5,698,019 A | 12/1997 | Frank et al. |
| 5,713,994 A | 2/1998 | Kramer et al. |
| 5,723,007 A | 3/1998 | Engel et al. |
| 5,727,943 A | 3/1998 | Beaty et al. |
| 5,755,809 A | 5/1998 | Cohen et al. |
| 5,759,036 A | 6/1998 | Hinds |
| 5,762,500 A | 6/1998 | Lazarof |
| 5,772,438 A | 6/1998 | Deom |
| 5,775,912 A | 7/1998 | Panzera et al. |
| 5,785,524 A | 7/1998 | Wolf |
| 5,833,463 A | 11/1998 | Hurson |
| 5,833,464 A | 11/1998 | Foser |
| 5,839,900 A | 11/1998 | Billet et al. |
| 5,843,348 A | 12/1998 | Giordano |
| 5,849,068 A | 12/1998 | Hofmann et al. |
| 5,873,721 A | 2/1999 | Willoughby |
| 5,910,273 A | 6/1999 | Thiel et al. |
| 5,915,967 A | 6/1999 | Clokie |
| 5,925,180 A | 7/1999 | Frank et al. |
| 5,931,674 A | 8/1999 | Hanosh et al. |
| 5,934,906 A | 8/1999 | Phimmasone |
| 5,939,211 A | 8/1999 | Mormann |

| | | | | | | |
|---|---|---|---|---|---|---|
| 5,947,732 | A | 9/1999 | Beaty et al. | 6,503,625 B1 | 1/2003 | Rieder et al. |
| 5,947,737 | A | 9/1999 | Billet et al. | 6,514,453 B2 | 2/2003 | Vigliotti et al. |
| 5,951,290 | A | 9/1999 | Ardizio et al. | 6,527,553 B2 | 3/2003 | Yeung |
| 5,951,293 | A | 9/1999 | Billet et al. | 6,540,784 B2 | 4/2003 | Barlow et al. |
| 5,951,295 | A | 9/1999 | Lyles et al. | 6,627,327 B2 | 9/2003 | Reidt et al. |
| 5,964,592 | A | 10/1999 | Hites et al. | 6,641,775 B2 | 11/2003 | Vigliotti et al. |
| 5,971,760 | A | 10/1999 | Letcher | 6,648,645 B1 | 11/2003 | MacDougald et al. |
| 5,975,905 | A | 11/1999 | Kim et al. | 6,666,684 B1 | 12/2003 | Names |
| 5,984,683 | A | 11/1999 | Sakata et al. | 6,669,476 B2 | 12/2003 | Prestipino et al. |
| 5,989,026 | A | 11/1999 | Rogers et al. | 6,679,701 B1 | 1/2004 | Blacklock |
| 5,989,027 | A * | 11/1999 | Wagner et al. ............ 433/173 | 6,689,202 B2 | 2/2004 | Panzera |
| 6,010,337 | A | 1/2000 | Billet et al. | 6,743,936 B1 | 6/2004 | Wellinghoff et al. |
| 6,012,923 | A | 1/2000 | Bassett et al. | 6,752,863 B2 | 6/2004 | Lyles et al. |
| 6,013,591 | A | 1/2000 | Ying et al. | 6,755,651 B2 | 6/2004 | Brodbeck |
| 6,027,742 | A | 2/2000 | Lee et al. | 6,787,584 B2 | 9/2004 | Jia et al. |
| 6,039,568 | A | 3/2000 | Hinds | 6,797,006 B2 | 9/2004 | Hodorek |
| 6,045,361 | A | 4/2000 | Misch et al. | 6,808,659 B2 | 10/2004 | Schulman et al. |
| 6,048,203 | A | 4/2000 | Rosenberg | 6,821,462 B2 | 11/2004 | Schulman et al. |
| 6,048,205 | A | 4/2000 | Wright | 6,846,181 B2 | 1/2005 | Karmaker et al. |
| 6,054,400 | A | 4/2000 | Brink et al. | 6,878,456 B2 | 4/2005 | Castro et al. |
| RE36,689 | E | 5/2000 | Beaty et al. | 6,881,488 B2 | 4/2005 | Giordano |
| 6,056,547 | A | 5/2000 | Names | 6,932,606 B2 | 8/2005 | Aravena et al. |
| 6,063,442 | A | 5/2000 | Cohen et al. | 6,945,448 B2 | 9/2005 | Medlin et al. |
| 6,080,692 | A | 6/2000 | Reise et al. | 6,949,251 B2 | 9/2005 | Dalal et al. |
| 6,087,553 | A | 7/2000 | Cohen et al. | 6,953,594 B2 | 10/2005 | Lee et al. |
| 6,117,456 | A | 9/2000 | Lee et al. | 6,976,999 B2 | 12/2005 | Charlebois et al. |
| 6,120,293 | A | 9/2000 | Lazzara et al. | 6,984,261 B2 | 1/2006 | Cummings et al. |
| 6,126,445 | A | 10/2000 | Willoughby | 6,986,660 B2 | 1/2006 | Kumar et al. |
| 6,126,732 | A | 10/2000 | Hofmann et al. | 7,011,522 B2 | 3/2006 | Panzera et al. |
| 6,135,775 | A | 10/2000 | Weisman | 7,291,012 B2 * | 11/2007 | Lyren ........................ 433/173 |
| 6,146,423 | A | 11/2000 | Cohen et al. | 7,718,100 B2 * | 5/2010 | Soler et al. ................ 264/16 |
| 6,152,737 | A | 11/2000 | Beaty et al. | 2001/0000486 A1 | 4/2001 | Story |
| 6,159,010 | A | 12/2000 | Rogers et al. | 2001/0051832 A1 | 12/2001 | Bakker et al. |
| 6,159,417 | A | 12/2000 | Giordano | 2002/0028424 A1 | 3/2002 | Prestipino et al. |
| 6,168,435 | B1 | 1/2001 | Beaty et al. | 2002/0039718 A1 | 4/2002 | Kwan |
| 6,168,436 | B1 | 1/2001 | O'Brien | 2002/0076673 A1 | 6/2002 | Wagner et al. |
| 6,168,633 | B1 | 1/2001 | Shoher et al. | 2002/0095213 A1 | 7/2002 | Bakker et al. |
| 6,183,256 | B1 | 2/2001 | Fisher et al. | 2002/0115742 A1 | 8/2002 | Trieu et al. |
| 6,183,515 | B1 | 2/2001 | Barlow et al. | 2002/0155412 A1 | 10/2002 | Panzera et al. |
| 6,186,791 | B1 | 2/2001 | Karmaker et al. | 2002/0160334 A1 | 10/2002 | Brodbeck |
| 6,193,516 | B1 | 2/2001 | Story | 2003/0031984 A1 | 2/2003 | Rusin et al. |
| 6,200,137 | B1 | 3/2001 | Holand et al. | 2003/0068598 A1 | 4/2003 | Vallittu et al. |
| 6,206,192 | B1 | 3/2001 | Winstead et al. | 2003/0073394 A1 | 4/2003 | Reidt et al. |
| 6,214,368 | B1 | 4/2001 | Lee et al. | 2003/0087984 A1 | 5/2003 | Erbe et al. |
| 6,224,662 | B1 | 5/2001 | Nemeth | 2003/0096214 A1 | 5/2003 | Luthardt et al. |
| 6,244,869 | B1 | 6/2001 | Billet et al. | 2003/0134925 A1 | 7/2003 | Guzauskas |
| 6,250,922 | B1 | 6/2001 | Bassett et al. | 2003/0148247 A1 | 8/2003 | Sicurelli et al. |
| 6,267,597 | B1 | 7/2001 | Kim | 2004/0024081 A1 | 2/2004 | Trieu et al. |
| 6,270,347 | B1 | 8/2001 | Webster et al. | 2004/0058299 A1 | 3/2004 | Molin et al. |
| 6,271,282 | B1 | 8/2001 | Giordano | 2004/0064192 A1 | 4/2004 | Bubb |
| 6,280,863 | B1 | 8/2001 | Frank et al. | 2004/0097627 A1 | 5/2004 | Vallittu et al. |
| 6,283,753 | B1 | 9/2001 | Willoughby | 2004/0106085 A1 | 6/2004 | Vallittu et al. |
| 6,287,341 | B1 | 9/2001 | Lee et al. | 2004/0106087 A1 | 6/2004 | Weigl et al. |
| 6,299,448 | B1 | 10/2001 | Zdrahala et al. | 2004/0131562 A1 | 7/2004 | Gower et al. |
| 6,306,784 | B1 | 10/2001 | Drescher et al. | 2004/0152034 A1 | 8/2004 | Cummings et al. |
| 6,322,728 | B1 | 11/2001 | Brodkin et al. | 2004/0170946 A1 | 9/2004 | Lyren |
| 6,325,628 | B1 | 12/2001 | Morgan | 2004/0197737 A1 | 10/2004 | Uckelmann et al. |
| 6,331,312 | B1 | 12/2001 | Lee et al. | 2004/0234925 A1 | 11/2004 | Benhamou |
| 6,342,302 | B1 | 1/2002 | Steidl et al. | 2004/0241614 A1 | 12/2004 | Goldberg et al. |
| 6,342,458 | B1 | 1/2002 | Schweiger et al. | 2005/0014108 A1 | 1/2005 | Wohrle et al. |
| 6,343,930 | B1 | 2/2002 | Beaty et al. | 2005/0023710 A1 | 2/2005 | Brodkin et al. |
| 6,345,984 | B2 | 2/2002 | Karmaker et al. | 2005/0028424 A1 | 2/2005 | Poinski |
| 6,354,836 | B1 | 3/2002 | Panzera et al. | 2005/0031704 A1 | 2/2005 | Ahn |
| 6,362,250 | B1 | 3/2002 | Karmaker et al. | 2005/0084533 A1 | 4/2005 | Howdle et al. |
| 6,362,251 | B1 | 3/2002 | Alkemper et al. | 2005/0084819 A1 | 4/2005 | Sims et al. |
| 6,379,153 | B1 | 4/2002 | Schroering | 2005/0084821 A1 | 4/2005 | Sims et al. |
| 6,386,876 | B1 | 5/2002 | Lee | 2005/0096652 A1 | 5/2005 | Burton |
| 6,394,806 | B1 | 5/2002 | Kumar | 2005/0100724 A1 | 5/2005 | Seargeant |
| 6,402,517 | B1 | 6/2002 | Hozumi et al. | 2005/0109060 A1 | 5/2005 | Cummings et al. |
| 6,419,491 | B1 | 7/2002 | Ricci et al. | 2005/0184134 A1 | 8/2005 | Charlebois et al. |
| 6,431,868 | B2 | 8/2002 | Story | 2005/0191248 A1 | 9/2005 | Hunter et al. |
| 6,439,890 | B1 | 8/2002 | Karmaker et al. | 2005/0221259 A1 | 10/2005 | Anderson |
| 6,447,549 | B1 | 9/2002 | Taft | 2005/0261795 A1 | 11/2005 | Ghosh et al. |
| 6,450,813 | B1 | 9/2002 | McDonald et al. | 2005/0266382 A1 | 12/2005 | Soler et al. |
| 6,451,292 | B2 | 9/2002 | Warford, III et al. | 2006/0075826 A1 | 4/2006 | Roberts et al. |
| 6,454,569 | B1 | 9/2002 | Hollander et al. | 2007/0015110 A1 | 1/2007 | Zhang et al. |
| 6,485,849 | B2 | 11/2002 | Petticrew | 2007/0111165 A1 | 5/2007 | Wallick et al. |
| 6,495,073 | B2 | 12/2002 | Bodenmiller et al. | 2007/0118221 A1 | 5/2007 | Robie et al. |
| 6,497,573 | B2 | 12/2002 | Wagner et al. | 2007/0148621 A1 | 6/2007 | Yakir |

| | | | |
|---|---|---|---|
| 2007/0184265 | A1 | 8/2007 | Ranganathan et al. |
| 2008/0050699 | A1 | 2/2008 | Zhang et al. |
| 2009/0036908 | A1 | 2/2009 | Zokol et al. |

FOREIGN PATENT DOCUMENTS

| | | |
|---|---|---|
| DE | 4209569 | 11/1994 |
| DE | 19529036 | 3/1997 |
| DE | 10105398 | 8/2010 |
| EP | 0266313 | 5/1988 |
| EP | 0345581 | 12/1989 |
| EP | 0366018 | 5/1990 |
| EP | 0417018 | 3/1991 |
| EP | 0467948 | 1/1992 |
| EP | 0498923 | 8/1992 |
| EP | 0333503 | 2/1993 |
| EP | 0806211 | 11/1997 |
| EP | 0271236 | 6/1998 |
| EP | 0950421 | 10/1999 |
| EP | 1281372 | 2/2003 |
| EP | 1598028 | 11/2005 |
| EP | 1712205 | 10/2006 |
| FR | 2796265 | 1/2001 |
| GB | 1526780 | 9/1978 |
| GB | 2401867 | 11/2004 |
| GB | 2416996 | 2/2006 |
| JP | 61275205 | 12/1986 |
| JP | 63290559 | 11/1988 |
| JP | 1025849 | 1/1989 |
| JP | 2002126071 | 5/2002 |
| WO | 8900410 | 1/1989 |
| WO | 9011979 | 11/1990 |
| WO | 9320773 | 10/1993 |
| WO | 9421190 | 9/1994 |
| WO | 9528973 | 11/1995 |
| WO | 9721393 | 6/1997 |
| WO | 9741809 | 11/1997 |
| WO | 9830170 | 7/1998 |
| WO | 0021455 | 4/2000 |
| WO | 0132072 | 5/2001 |
| WO | 0187193 | 5/2001 |
| WO | 0236039 | 5/2002 |
| WO | WO 02/34155 A1 * | 5/2002 |
| WO | 02062901 | 8/2002 |
| WO | 02064100 | 8/2002 |
| WO | 03065939 | 8/2003 |
| WO | 03065996 | 8/2003 |
| WO | 03078508 | 9/2003 |
| WO | 03094774 | 11/2003 |
| WO | 2004054464 | 7/2004 |
| WO | 2006082610 | 8/2006 |
| WO | 2007027794 | 3/2007 |
| WO | 2007086832 | 8/2007 |

OTHER PUBLICATIONS

Computer-Guided Immediate Provisionalization of Anterior Multiple Adjacent Implants: Surgical and Prosthodontic Rationale, Joseph Y. K. Kan, Practical Procedures & Aethetic Dentistry, vol. 18, No. 10, 617-623, 2006.

Flocculants, Binders, and Bonds, Chapter 11, Molecular Binders pp. 173-177, 1995.

Injection Molding, Chapter 24, Equipment and Material Variables in Injection Molding, pp. 479-481.

Innovative Ceramic-Fiber Technology Energizes Advanced Cerametrics, Richard B. Cass et al. Story—the American Ceramic Society, American Ceramics Society Bulletin, Nov. 2003, pp. 9701-9706.

PEEK-CLASSIX, Information Sheet Invibio Ltd., Properties of PEEK-CLASSIX White Granular, Nov. 2003.

Presurgical Planning With CT-Derived Fabrication of Surgical Guides, Scott D. Ganz, J Oral Maxillofac Surg 63:59-73, 2005, Suppl 2.

Prosthetically Directed Implant Placement ing Computer Software to Ensure Precise Placement and Predictable Prosthetic Outcomes. Part 1: Diagnostics, Imaging, and Collaborative Accountability, Alan L. Rosenfeld, International Journal of Periodontics & Restorative Dentistry, vol. 26, No. 3, 2006, 215-221.

Shape Optimization of Randomly Oriented Short Fibers for Bone Cement Reinforcements, Van Zhou, Chaodi Li, James J. Mason, Materials Science & Engineering A 393 (2005) 374-381.

The Clinical Assessment of a Ceramic-Coated Transmucosal Dental Implant Collar; International Journal of Prosthodontics; 1996—vol. 9, Issue 5; pp. 466-472.

Two Applications of Transmucosal Milled Ceramic in Implantology; Preliminary Clinical Examples; Implant Quintessence Dentistry International; Aug. 1996—vol. 27, Issue 8, pp. 533-547.

International Search Report from related application PCT/ 2006/ 033893, dated Jan. 29, 2007, 1 page.

International Search Report from related application PCT/ 2006/ 020130, dated Feb. 6, 2007, 10 pages.

International Search Report from related application PCT/ 2007/ 069562, dated Jul. 7, 2008, 1 page.

International Search Report from related application PCT/ 2008/ 074616; dated Dec. 16, 2008; 4 pages.

International Search Report from related application PCT/ 2008/ 074645, dated Dec. 29, 2008; 9 pages.

International Search Report from related application PCT/ 2008/ 074642; dated Feb. 12, 2009, 4 pages.

International Search Report from related application PCT/ 2008/ 074655; dated Feb. 18, 2009, 9 pages.

International Search Report from related application PCT/ 2009/ 048469, dated Oct. 19, 2009, 9 pages.

International Search Report from related application PCT/ 2009/ 048476; dated Dec. 10, 2009; 13 pages.

International Search Report from related application PCT/ 2009/ 048481; dated Dec. 10, 2009; 13 pages.

International Search Report from related application PCT/ 2009/ 062308; dated Jan. 21, 2010; 17 pages.

International Search Report from related application PCT/ 2009/ 048456; dated Apr. 27, 2010; 5 pages.

* cited by examiner

FIG_1

FIG_2

FIG_7

DENTAL IMPLANT WITH IMPROVED OSSEOINTEGRATION FEATURES

CROSS-REFERENCE TO RELATED APPLICATIONS

This application claims the benefit of U.S. Provisional Patent Application No. 60/712,577, filed Aug. 30, 2005, which is incorporated herein by reference in its entirety.

BACKGROUND OF THE INVENTION

1. Field of the Invention

The present invention relates to dental implants and, in particular, to a dental implant with improved osseointegration features.

2. Description of the Related Art

Dental implants are commonly used as anchoring members for dental restorations to provide prosthetic teeth at one or more edentulous sites in a patient's dentition at which the patient's original teeth have been lost or damaged. Typically, known implant systems include a dental implant made from a suitable biocompatible material, such as titanium. The dental implant is typically threaded into a bore which is drilled into the patient's mandible or maxilla at the edentulous site. The implant provides an anchoring member for a dental abutment, which in turn provides an interface between the implant and a dental restoration. The restoration is typically a porcelain crown fashioned according to known methods.

Many current dental implant surgeries are performed in two stages. In the initial or first stage, an incision is made in the patient's gingiva at an edentulous side, and a bore is drilled into the patient's mandible or maxilla at the edentulous site, followed by threading or impacting a dental implant into the bore using a suitable driver. Thereafter, a cap is fitted onto the implant to close the abutment coupling structure of the implant, and the gingiva is sutured over the implant. Over a period of several months, the patient's jaw bone grows around the implant to securely anchor the implant in the surrounding bone, a process known as osseointegration.

In a second stage of the procedure following osseointegration, the dentist reopens the gingiva at the implant site and secures an abutment and optionally, a temporary prosthesis or temporary healing member, to the implant. Then, a suitable permanent prosthesis or crown is fashioned, such as from one or more impressions taken of the abutment and the surrounding gingival tissue and dentition. In the final stage, the temporary prosthesis or healing member is removed and replaced with the permanent prosthesis, which is attached to the abutment with cement or with a fastener, for example.

Although the osseointegration of existing dental implants into surrounding bone has proven adequate, further improvements in osseointegration of dental implants are desired.

SUMMARY OF THE INVENTION

The present invention provides a dental implant which is made at least in part of a highly porous biomaterial such as porous tantalum for enhancing the osseointegration of the dental implant into surrounding bone. In one embodiment, a dental implant is provided which includes a core formed of titanium, for example, the core including a head portion having an abutment interface and a stem portion extending from the head portion. A porous tantalum sleeve is disposed about the stem portion and occupies a substantial portion of the implant/bone interface of the implant. After implantation of the implant, bone tissue may osseointegrate into the porous tantalum sleeve to anchor the implant in position within the surrounding bone. Other embodiments of implants are provided, each implant including at least a portion thereof formed of porous tantalum for improved osseointegration.

In one form thereof, the present invention provides a dental implant, including a core, and at least one porous tantalum portion connected to the core. The dental implant may further include a head portion including an abutment interface, and a stem portion projecting from the head portion. The porous tantalum portion may include a sleeve disposed about the stem portion of the core. The core may further include an abutment portion integrally formed with the core.

In another form thereof, the present invention provides a dental implant, including a body formed substantially of porous tantalum, and a bore extending at least partially into the body. The body may further include an outer surface and at least one rib extending from the outer surface.

In other alternative aspects of the embodiments described herein, the core may have a protrusion, such as a helical thread, extending though the porous body. In another alternative, the porous body may have reinforcement, such as reinforcing members, extending within the body, and which may or may not be connected to a head portion of the dental implant. In one form, the head portion is configured to be press-fit onto the porous body.

BRIEF DESCRIPTION OF THE DRAWINGS

Corresponding reference characters indicate corresponding parts throughout the several views. The exemplifications set out herein illustrate preferred embodiments of the invention, and such exemplifications are not to be construed as limiting the scope of the invention in any manner.

DETAILED DESCRIPTION

Figure 1:
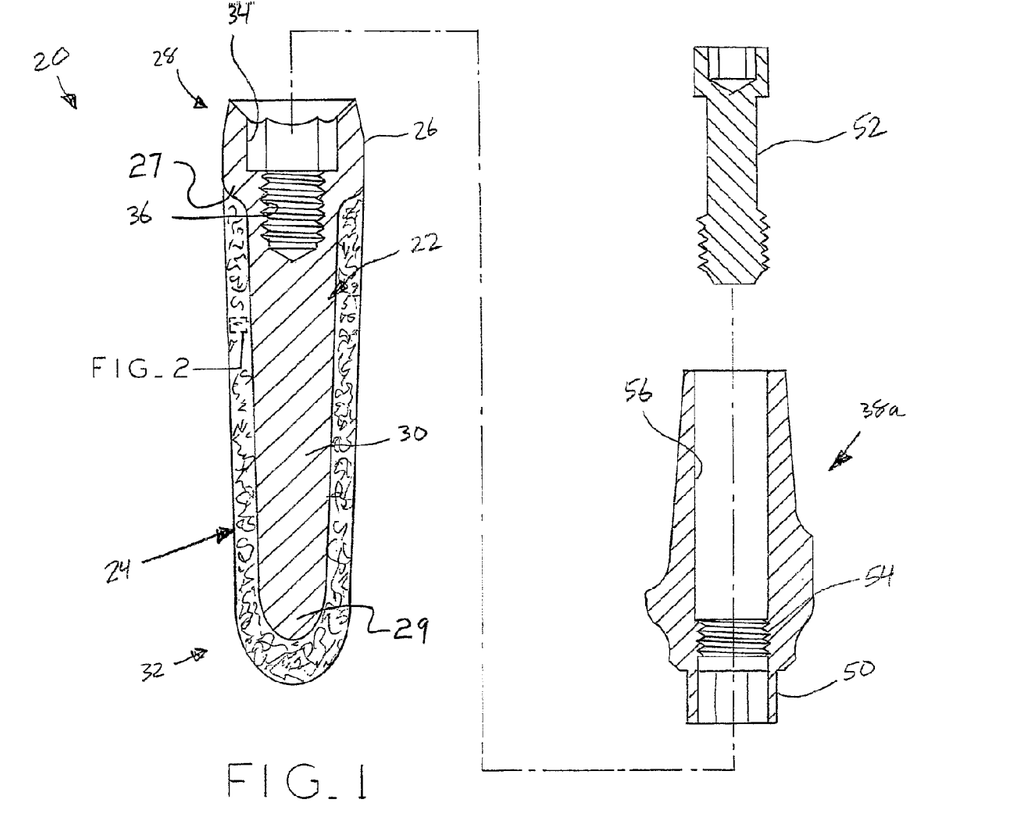
FIG. 1 is an exploded sectional view of a dental implant system including a dental implant with a core and a sleeve of porous tantalum, an abutment, and an abutment screw.
Figure 10A:
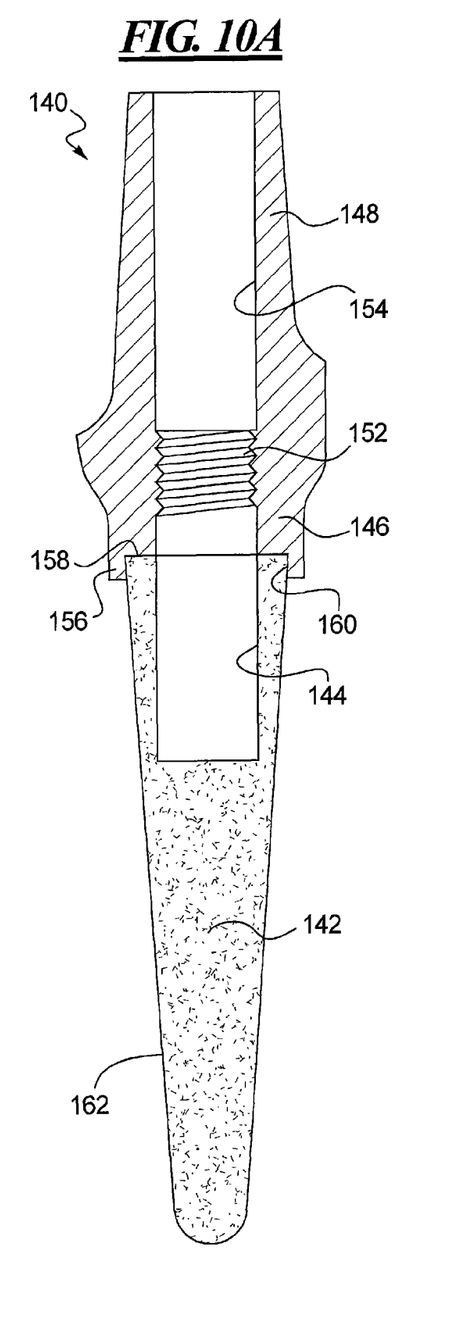
FIGS. 10A and 10B are cross-sectional alternate forms of a seventh embodiment of a dental implant, further showing a head portion press-fit onto a porous implant body.
Figure 10B:
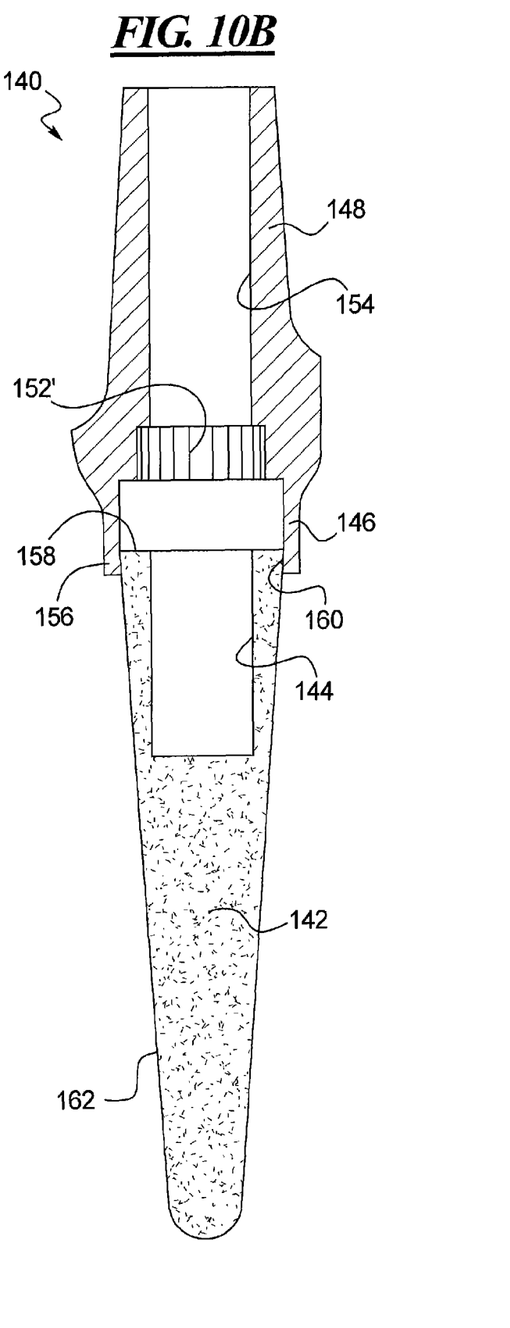

Referring to FIG. 1, there is illustrated a dental implant 20. Implant 20 may be cylindrical in shape or may be tapered in shape. Implant 20 generally includes a core 22 made of a suitable biocompatible material, such as titanium, and a sleeve 24 made of porous tantalum, as described below. Core 22 generally includes head portion 26 at a coronal, or proximal end 28 of implant 20, and stem portion 30 projecting from head portion 26 toward an apical, or distal end 32 of implant 20, wherein stem portion 30 is somewhat reduced in width or profile (cross-sectional) in comparison with head portion 26. Head portion 26 of core 22 additionally includes an abutment interface structure, shown herein as an internal hex 34 and an internally threaded bore 36 for attaching a dental abutment 38a to implant 20 in the manner described below. Although the abutment interface structure between implant 20 and abutment 38 is shown herein as an internal hex 34 within implant 20 which receives an external hex of abutment 38a as described below, the foregoing arrangement may be reversed. Also, many other types of implant/abutment interfaces are well known in the art, such as splines as represented in FIG. 10 in dashed line and shown in U.S. Pat. No. 5,449,291, the disclosure of which is hereby incorporated by reference, or other geometric shapes such as octagons, lobes, and other shapes.

Sleeve 24 is secured to core 22 in a suitable manner, such as via a cement or by sintering sleeve 24 to core 22, for example. As shown herein, sleeve 24 interfaces with the lower end 27 of head portion 26 of core 22, substantially encapsulates stem portion 30 of core 22, and extends distally below the end 29 of stem portion 30 of core 22. In this manner, a substantial portion of the bone interface or bone-contacting portion of implant 20 from proximal end 28 to distal end 32 thereof is formed by sleeve 24.

Sleeve 24 is formed of a highly porous biomaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium, or alloys of tantalum and niobium with one another or with other metals may also be used.

Figure 2:
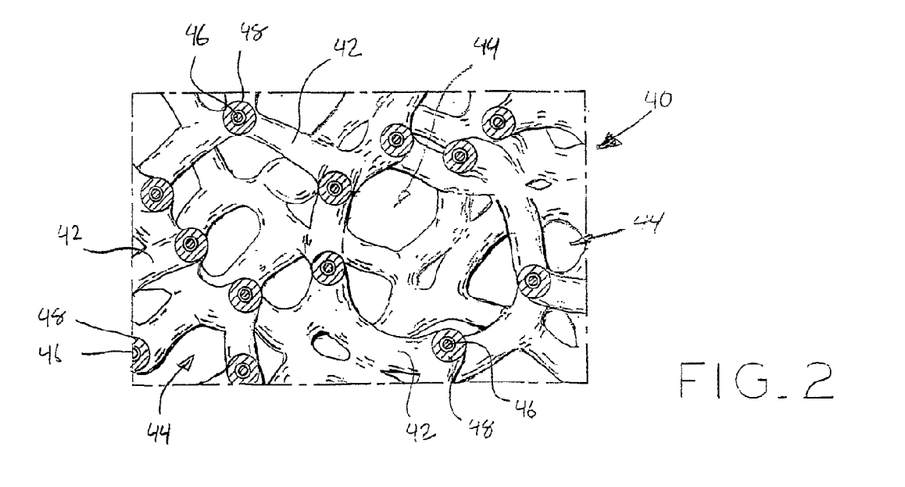
FIG. 2 is an enlarged fragmentary view of a portion of the porous tantalum sleeve of the implant of FIG. 1, showing the porous tantalum structure.

Generally, as shown in FIG. 2, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 20 into the surrounding bone of a patient's jaw.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

In use, implant 20 may be fitted into a bore (not shown) drilled into a patient's jaw bone at an edentulous site. In particular, implant 20 may be impacted or press-fitted into the bore to provide a firm initial seating of implant 20 into the bore. Thereafter, the bone tissue surrounding implant 20 may osseointegrate into the open spaces 44 of the porous tantalum of sleeve 24, thereby firmly anchoring sleeve 24 and implant 20 into the surrounding bone structure. At a later stage following osseointegration, an abutment 38a may be secured to implant 20 by fitting an external hex 50 of abutment 38a into internal hex 34 of core 22 of the implant, followed by threading abutment screw 52 through a screw retaining thread 54 within central bore 56 of abutment 38a and into threaded bore 36 of implant 20 to securely attach abutment 38a to implant 20. Thereafter, a temporary or permanent prosthesis (not shown) may be secured to abutment 38a in a known manner.

Optionally, implant 20, as well as the other implants described below, may have multiple textured surfaces as described in detail in U.S. Pat. No. 5,989,027, assigned to the assignee of the present invention, the disclosure of which is expressly incorporated herein by reference. For example, sleeve 24 of porous tantalum may have an increasing porosity from proximal end 28 toward distal end 32 of implant 20. Sleeve 24 could be formed of substantially solid, non-porous porous tantalum near proximal end 28 of implant 20 to provide a seal with the surrounding gingiva such that plaque or bacteria cannot lodge on or deposit within sleeve 24 near the gumline of the patient should the upper portion of sleeve 24 be exposed to the oral cavity. Alternatively, the surface of head portion 26 of core 22 could be formed of smooth, polished titanium to allow ready removal of bacterial plaque deposits by conventional oral hygiene techniques in the event that head portion 26 of implant 20 becomes exposed to the oral cavity. The porosity of the porous tantalum structure 40 of sleeve 24 could increase along the length of sleeve 24 toward distal end 32 of implant 20 to promote maximum bone ingrowth and osseointegration of implant 20 along implant 20 toward distal end 32 thereof. More specifically, the porous tantalum structure 40 of sleeve 24 could be formed with a gradient of increasing porosity from proximal end 28 toward distal end 32 of implant 20, wherein the open or void spaces 44 within the porous tantalum structure 40 become larger from proximal end 28 to distal end 32 of implant 20.

Also, sleeve 24 may be attached to core 22 of implant 20 in a manner wherein, after osseointegration of sleeve 24 into the surrounding bone, core 22 is slightly movable relative to sleeve 24 in order to dissipate forces which are imposed upon implant 20, such as mastication forces, for example. In one embodiment, sleeve 24 may be secured to core 22 via an adhesive material which is slightly compressible, such that when mastication or other forces are imposed upon head portion 26 of implant via the prosthesis and abutment, head portion 26 and/or stem portion 30 of core 22 of implant 20 may move slightly relative to sleeve 24. In other embodiments, a compression ring, a spring, or another type of "shock absorbing" structure may be fitted between core 22 and sleeve 24 to allow for relative movement therebetween.

Figure 3:
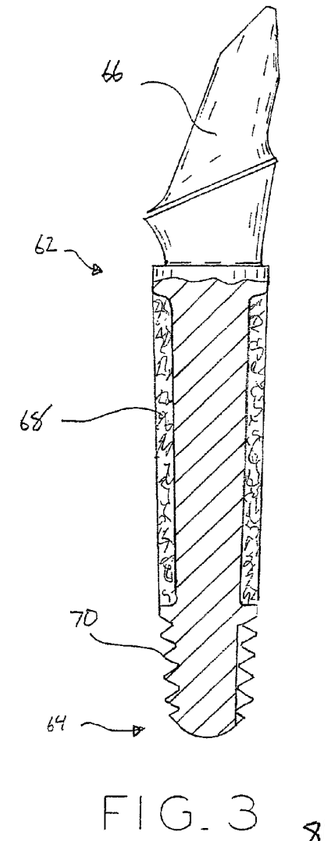
FIG. 3 is a partial cross-sectional view of a second embodiment of a dental implant, the dental implant including an implant body and an integral abutment portion.

Referring to FIG. 3, there is illustrated a second embodiment of an implant. Implant 60 according to another embodiment of the present invention is shown as a "single-piece" implant which includes both an implant body and an integral abutment portion. Implant 60 may be formed of titanium, for example, and the body thereof includes proximal end 62 and distal end 64, with abutment portion 66 integrally formed with implant 60 and projecting from proximal end 62 of implant 60. Implant 60 includes sleeve 68 of porous tantalum disposed therearound, similar to implant 20 of FIG. 1 discussed above. Distal end 64 of implant 60 includes a thread 70 for initial anchoring or securement of implant 60 within a bore (not shown) drilled into the jaw bone of a patient. After initial anchoring of implant 60 into the bore via thread 70, a temporary prosthesis (not shown) may be secured to abutment portion 66 while a final prosthesis is fashioned. The bone-engaging portion of implant 60 may be generally cylindrical or may be tapered.

Figure 4:
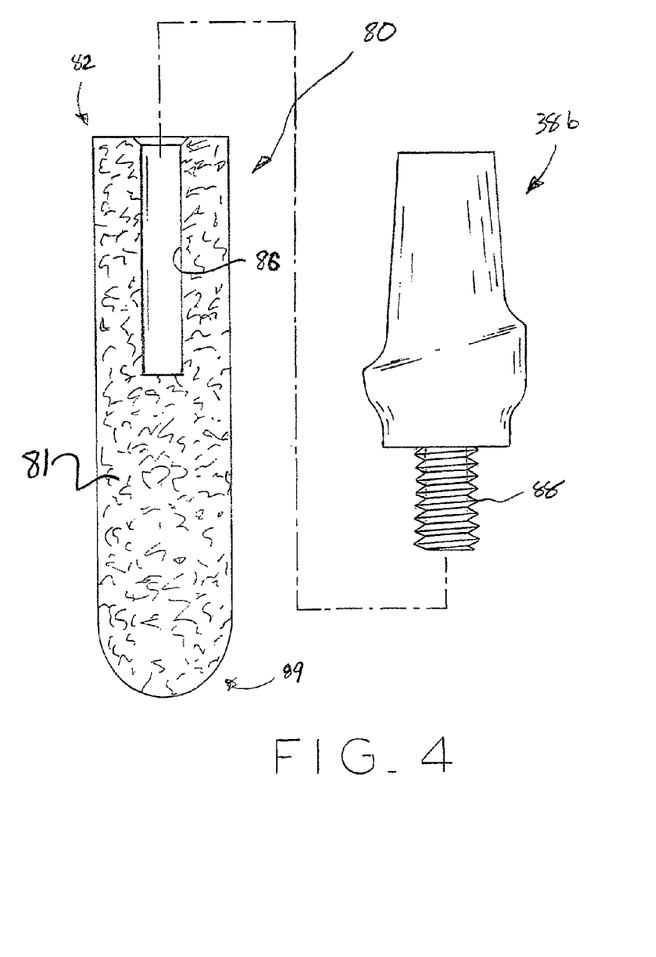
FIG. 4 is a cross-sectional view of a third embodiment of a dental implant and an elevational view of an abutment.
Figure 5:
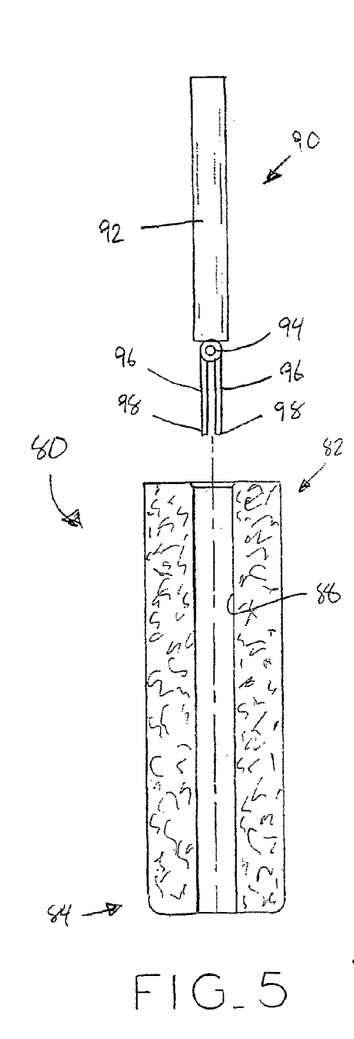
FIG. 5 is a cross-sectional view of the dental implant of FIG. 4 and an elevational view of an anchor member.

Referring to FIG. 4, there is illustrated a third embodiment of an implant. Implant 80 includes a generally cylindrical or bullet-shaped body portion 81 formed substantially entirely of porous tantalum. Implant 80 may also be tapered in shape. Implant 80 includes proximal end 82, distal end 84, and a central bore 86 extending from proximal end 82 partially into implant 80 towards distal end 84 thereof. Alternatively, as shown in FIG. 5 and discussed below, central bore 86 may extend entirely through implant 80 to distal end 84. Implant 80 may be screwed or torqued into a bore (not shown) drilled in a patient's jaw bone followed by allowing the surrounding bone tissue to osseointegrate into the porous tantalum of implant 80. When it is desired to secure abutment 38*b* to implant 80, threaded shaft 88 of abutment 38*b* may be threaded into central bore 86 of implant 80, wherein the threads of threaded shaft 88 of abutment 38*b* tap directly into the porous tantalum material surrounding central bore 86 to provide a rigid connection therebetween which is resistant to pull-out of abutment 38*b* from implant 80. Optionally, bore 86 of implant 80 may include a threaded metal sleeve in which threaded shaft 88 of abutment 38*b* may be threaded. Thereafter, osseointegration of surrounding bone tissue into and around the porous tantalum of implant 80 and threaded shaft 88 of abutment 38*b* further integrates implant 80 into the surrounding bone structure and also enhances the connection of abutment 38*b* to implant 80.

Figure 6:
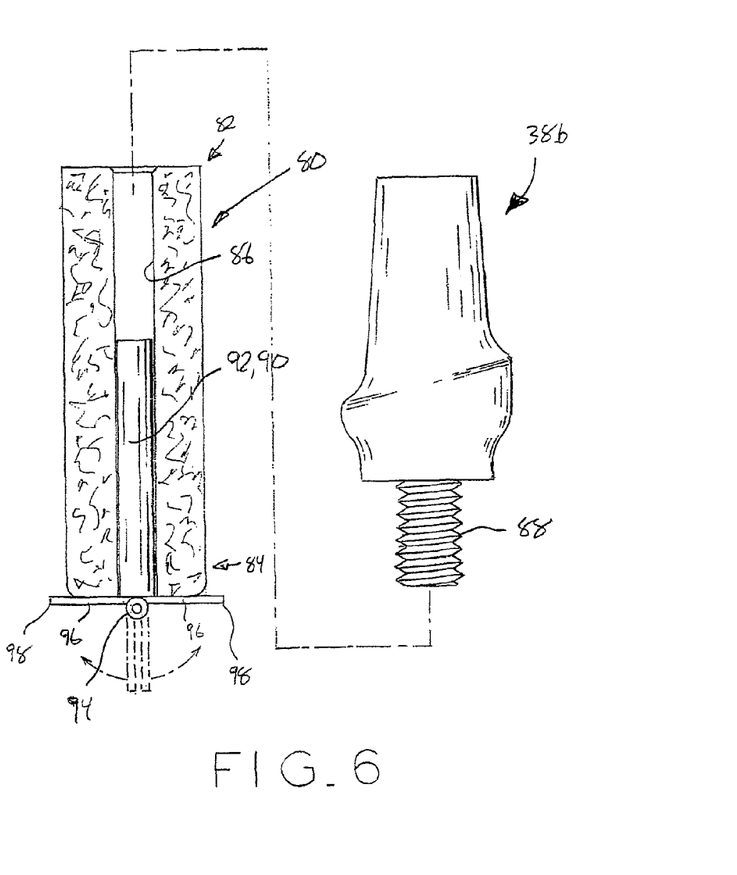
FIG. 6 is a continuation of FIG. 5, showing deployment of the anchor member, and further showing an abutment.

Referring to FIGS. 5 and 6, an anchor member 90 is shown which may optionally be used with implant 80. Anchor member 90 includes central shaft 92, a spring-loaded pivot joint 94, and a pair of anchor arms 96. After implant 80 is impacted into a bore (not shown) in a patient's jaw bone, anchor member 90 is driven through central bore 86 of implant 80 with anchor arms 96 in a retracted position as shown in FIG. 5, until anchor arms 96 clear distal end 84 of implant 80 externally of central bore 86. Thereafter, anchor arms 96 pivot at pivot joint 94 under the spring-loaded tension of pivot joint 94 to an extended position in which same are oriented in an opposed fashion perpendicular to the longitudinal axis of implant 80, such that the ends 98 of anchor arms 96 engage the bone within the bore in the patient's jaw bone. In this manner, anchor arms 96 provide an initial resistance to pull-out of implant 80 from the bore. Thereafter, after osseointegration of implant 80 into the surrounding bone tissue, abutment 38*b* may be secured by threading it into central bore 86 of implant 80 as described above. In addition to the spring-loaded anchor member embodiment described herein, other embodiments may be employed with other arrangements for providing additional anchoring to the implant.

Figure 7:
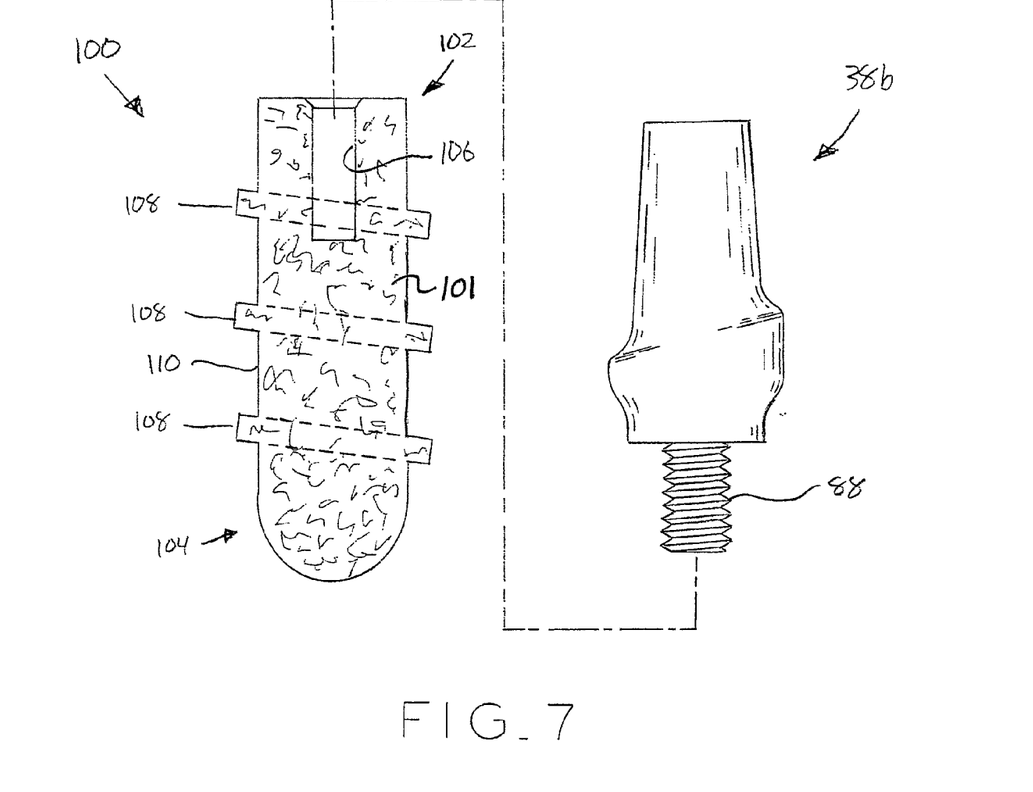
FIG. 7 is cross-sectional view of a fourth embodiment of a dental implant and an elevational view of an abutment.

Referring to FIG. 7, there is illustrated a fourth embodiment of an implant. Implant 100 includes a substantially cylindrical or bullet-shaped body 101 made substantially entirely of porous tantalum. Implant 100 also may be tapered in shape. Implant 100 includes proximal end 102, distal end 104, and a blind bore 106 extending partially into implant 100 from proximal end 102 thereof. Implant 100 additionally includes one or more ribs 108 protruding from the outer surface 110 thereof, wherein ribs 108 may be provided in the form of a single helical rib, or a plurality of annular ribs. In use, implant 100 is impacted into a bore (not shown) drilled into a patient's jaw bone, with ribs 108 engaging the surrounding bone to provide an initial resistance to pull-out of implant 100 from the bore before osseointegration of the implant 100 into the surrounding bone. Abutment 38*b* may be secured to implant 100 in the manner described above with respect to the embodiments of FIGS. 4-6 by threading threaded shaft 88 of abutment 38*b* directly into the porous tantalum surrounding blind bore 106 of implant 100. Optionally, blind bore 106 of implant 100 may include a threaded metal sleeve in which threaded shaft 88 of abutment 38*b* may be threaded.

Figures 8, 9:
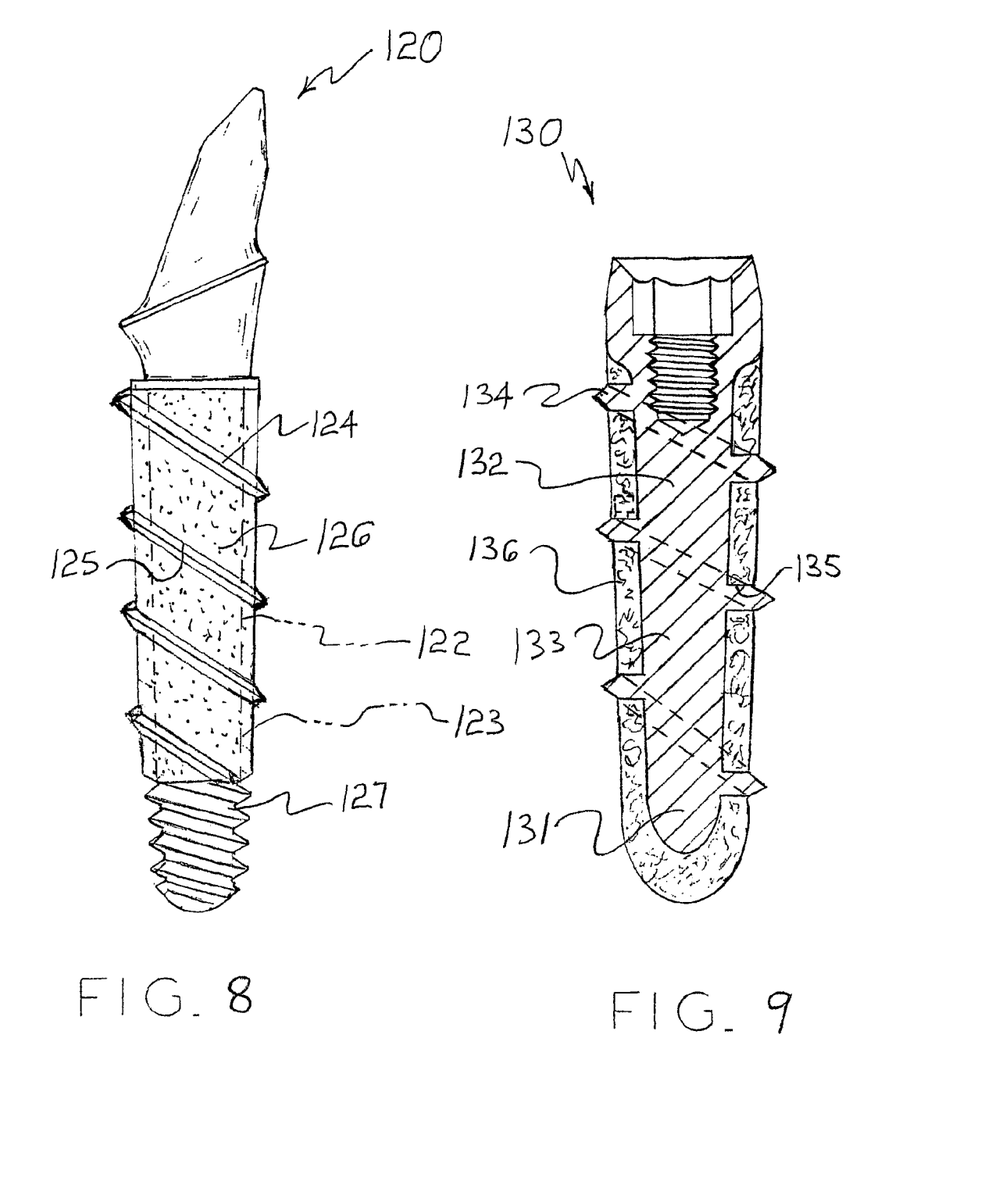
FIG. 8 is an elevational view of a fifth embodiment of a dental implant, and showing a thread protruding through a porous portion of the dental implant.
FIG. 9 is a cross-sectional view of a sixth embodiment of a dental implant, and showing a thread protruding through a porous portion of the dental implant.

Referring to FIGS. 8-9, there are illustrated a fifth and sixth embodiment, respectively. Implant 120 is constructed similarly to implant 60 (FIG. 3), while implant 130 is instructed similarly to implant 20 (FIG. 1). Thus, implants 120 and 130 have structure for connecting a porous body to abutments as described previously for implants 20 and 60. Also, implant 120 has a core 122 with a stem portion 123 (shown mainly in dashed line) extending within a preferably tantalum, porous portion or sleeve 126 similar to sleeve 68 on implant 60. The core 122 extends below the sleeve 126 to form cutting threads 127 like threads 70 on a distal end portion of the implant 60. Additionally, implant 130 has a porous sleeve 136 that covers both a stem portion 133 and a distal or apical end portion 131 of a core 132 similar to sleeve 24 of implant 20.

Here, however, the cores 122 and 132 have protrusions 124 and 134 that extend through respective sleeves 126 and 136 in order to facilitate cutting into the bone upon insertion of the implant into a bore on the jaw bone (not shown) and/or to aid in resistance to pull-out from the bore. The protrusions 124 and 134 preferably are helical ribs or threads 128 and 138 that extend respectively along stem portions 123 and 133. The threads 128 and 138 respectively extend through helical openings 125 and 135 on the sleeves 126 and 136. The helical threads 128 and 138 may extend past the porous sleeves 126 and 136 on the core of the implant, and may extend only in portions of the openings 125 and 136 on the sleeves 126 and 136 whether continuously or in separated segments along the helical path formed by the openings.

Referring to FIGS. 10A and 10B, a pair of seventh alternative embodiments of a dental implant are illustrated. The two alternative embodiments are identical in all respects except for the elements 152, 152', as will be explained herein. Dental implant 140 has a body 142 substantially made of a porous material, such as tantalum, similar to body 81 of the dental implant 80 (FIG. 4). The body 142 may include a bore 144 for attachment to an abutment connector 146. The bore 144 may be a blind bore or may have a threaded sleeve, as explained for body 81.

The abutment connector 146 covers a proximal or coronal surface 158 of the body 142 and may be provided with a number of different configurations to connect to an abutment. In one form, the abutment connector 146 may have an integral abutment and a threaded shank (not shown) received by the bore 144, similar to abutment 38*b* for implant 80. Alternatively, the abutment connector 146 may have an integral abutment 148 similar to abutment 38*a* with a bore 154 that includes a threaded portion 152 (FIG. 10A), analogous to bore 36 for receiving a retaining screw similar to screw 52, both as shown in FIG. 1. In yet another alternative, the abutment connector 146 may be separate from the abutment and may have abutment interface structure including anti-rotational structure such as the splined structure 152' (shown in FIG. 10B), the hex structure or others mentioned herein for engaging an abutment. These structures also may use a bore 154 for receiving the retaining screw. Whether the abutment connector 146 has an integral abutment or not, bore 154 on the abutment connector 146 aligns with bore 144 on the body 142 so that both bores can receive the retaining screw to secure the abutment connector 146 and abutment (if separate) to the body 142.

In order to create a tight fit or press-fit connection between the porous body 142 and the abutment connector 146, the connector 146 has a distally extending flange 156 that forms an opening 160. The flange 156 is preferably circular but may be other shapes to match the periphery of the coronal surface 158 of the body 142. So configured, the body 142 is connected to the abutment connector 146 by pressing the coronal end portion or surface 158 of the body 142 into opening 160. While the illustrated and preferred embodiments show that the press-fit connection may be provided in addition to other connecting structures between body 142 and connector 146, such as by retaining screw, threaded shank, reinforcing members (described below), fusion welding or adhesives, it should be understood that the press-fit connection may be the sole connection between the abutment connector 146 and the porous body 142.

In another aspect of this embodiment, body 142 is provided with a varying cross-sectional dimension so that a tapered outer surface 162 extends inwardly as it extends distally. The tapered surface 162 limits interference with the roots of adjacent teeth, and helps to redirect and dissipate compressive forces, generated from mastication, into transverse or lateral directions relative to a longitudinal axis of the implant. The tapered surface 162 also assists in aligning the implant with a bore on the jaw bone as it is being inserted into and through the bore.

Referring now to FIGS. 11A, 11B, 12A, and 12B, there are illustrated a pair of eighth alternate embodiments of an implant. The two alternative embodiments are identical in all respects except for element 188 of FIGS. 11B and 12B, as will be explained herein. Implant 170 has embedded reinforcing 171 to strengthen a substantially porous body 172. These reinforcements may be placed at the locations of greatest stress to provide the maximum amount of strengthening to the implant. These locations may be near the center of or may be near the outer diameter of the implant. The body 172 has a material as described above for the body 81 of implant 80. Implant 170 also has an abutment connector 174 disposed on a coronal end 176 of the body 172. The abutment connector 174 is not particularly limited to a specific abutment-connecting configuration. For implant 170, reinforcement 171 includes a plurality of reinforcing members 178, 180, 182 and 184 generally aligned with, and preferably offset radially from, central longitudinal axis C of the body 142'. In one form, the reinforcing members 178, 180, 182, 184 are elongated bars and may be made of the same or similar material to that of the abutment connector 174 and core 22 (FIG. 1) mentioned above, which includes titanium. The members 178, 180, 182, 184 are uniformly spaced about the axis C and generally extend in a coronal-apical or superior-inferior direction. With this structure, the reinforcing members 178, 180, 182, and 184 dissipate compressive forces impacting on the implant from mastication. In the current embodiment, the reinforcing members 178, 180, 182, and 184 extend from the abutment connector 174 in order to provide further anchoring the abutment connector 174 to the porous body 172. In this case, the members 178, 180, 182 and 184 may be integrally formed with, welded or otherwise connected to the abutment connector. This results in the direct transmission of impact forces from the abutment connector 174 to the reinforcing members 178, 180, 182, and 184, which further aids in dissipating the forces.

Figure 11A:
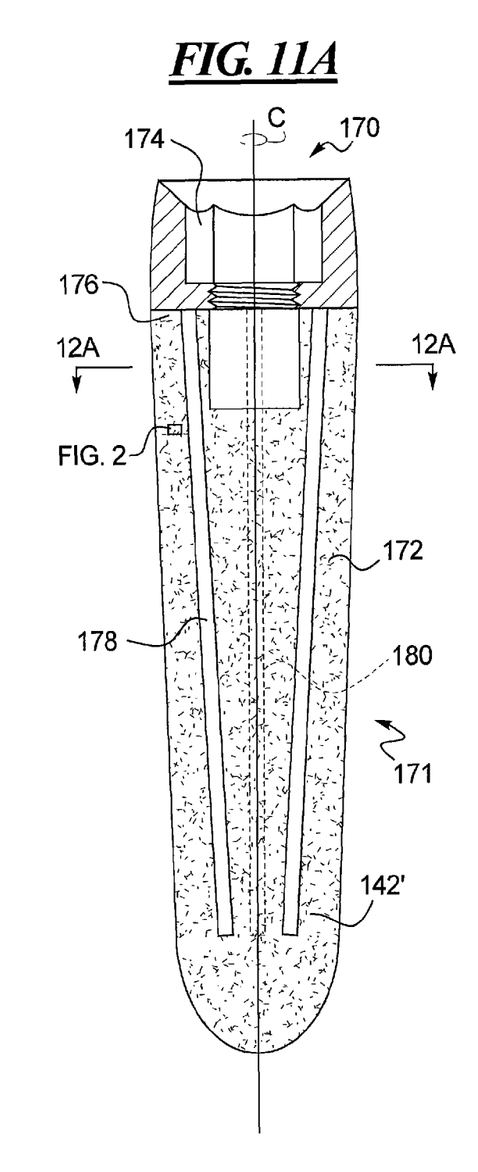
FIGS. 11A and 11B are cross-sectional alternate forms of an eighth embodiment of a dental implant, including a porous portion of the dental implant with off-center reinforcements.
Figure 11B:
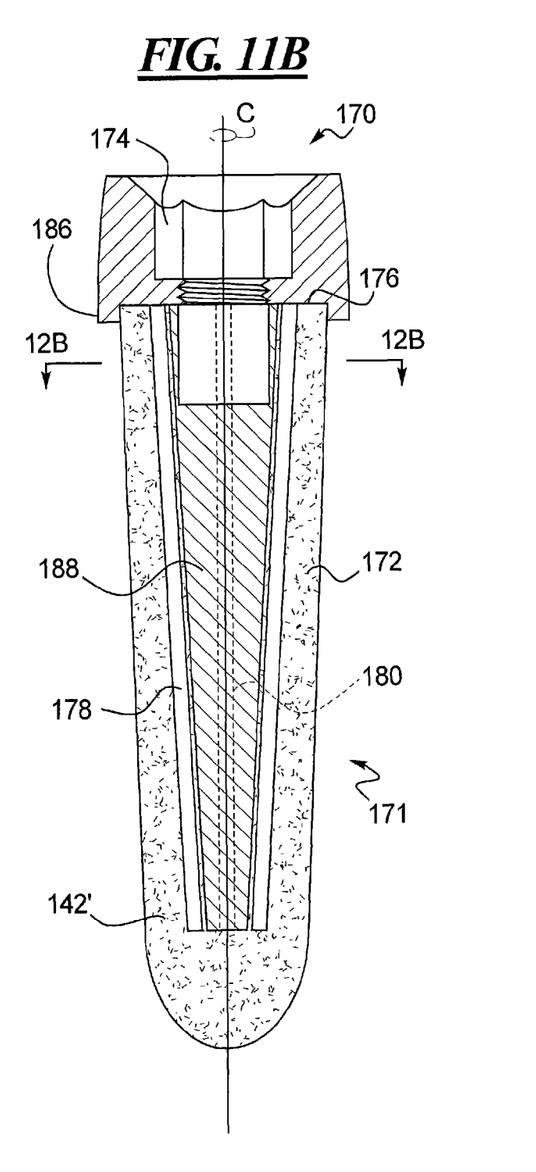

The abutment connector 174 also may be provided with a depending flange 186 (as shown in FIG. 11B) similar to flange 156, and the connector 174 may be appropriately sized, in order to provide a press-fit connection between the connector 174 and porous body 172, as described for implant 140.

Figure 12A:
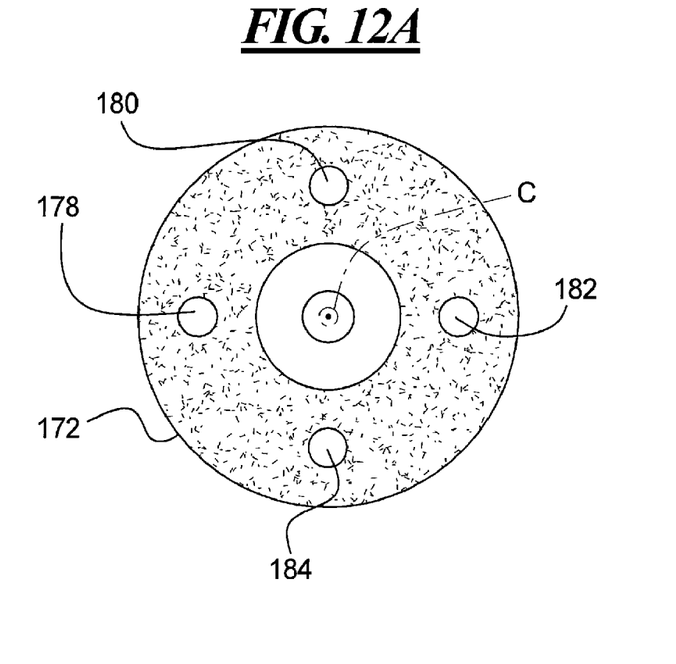
FIGS. 12A and 12B are across-sectional views taken along lines 12A-12A and 12B-12B, respectively, of the dental implant of FIGS. 11A and 11B.
Figure 12B:
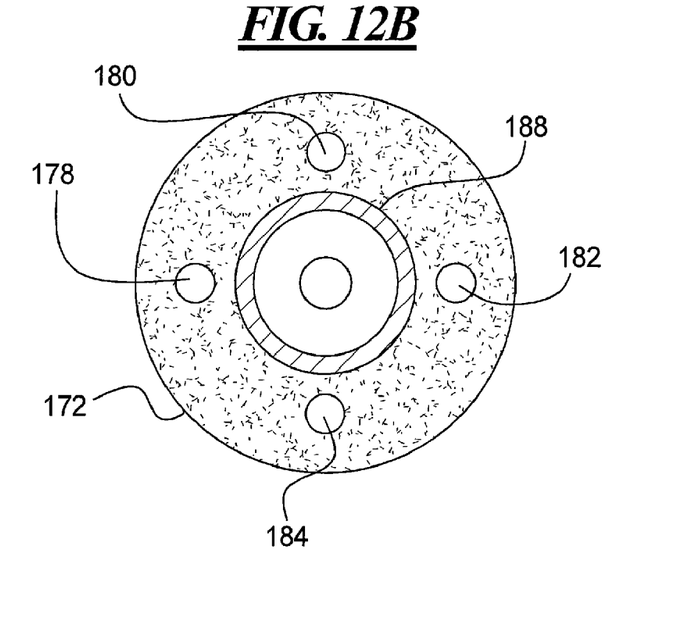

As another alternative configuration, in addition to the reinforcing 171, the abutment connector 174 may be a portion of a central core 188 (as shown in FIGS. 11B and 12B) that is provided to increase the strength of the implant 170. As shown in FIG. 11B, the core 188 extends downwardly from the abutment connector 174 and into a region near the apical end of the body 172. The reinforcing members 178, 180, 182, and 184 are generally aligned with, and spaced radially inward from, the core 188 and angled inward toward the core 188 proceeding from the coronal end toward the apical end.

Figure 13:
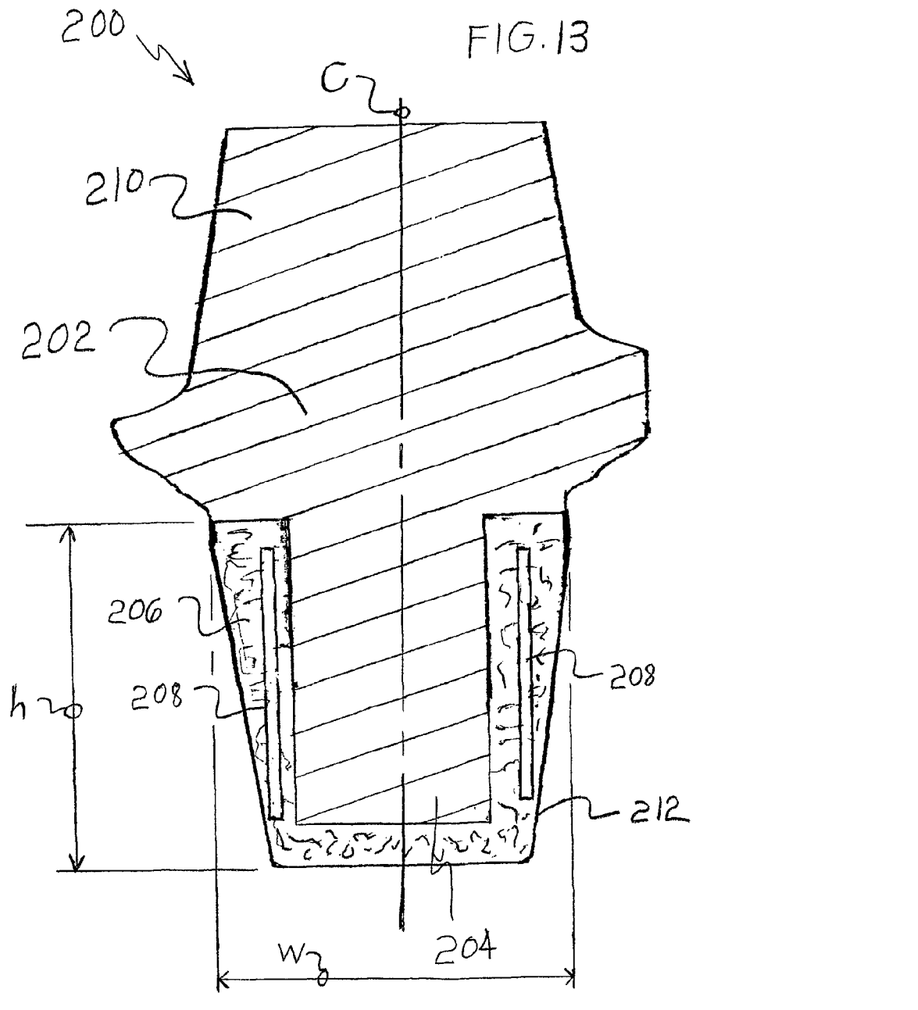
FIG. 13 is a cross-sectional view of a ninth embodiment of a dental implant, and showing an implant body with a central core and multiple off center cores.

Referring now to FIG. 13, there is illustrated another dental implant 200 with both a core and additional reinforcing. The implant 200 has an abutment connector 202 shown with an integral abutment 210 as one example abutment-connecting configuration. The abutment connector 202 has an enlarged central core 204 that extends into a porous body 206. The body 206 also has reinforcing members 208. The combination of reinforcing members 208 and core 204 provide substantial strength to compensate for significant bone loss in the jaw as occurs with geriatric patients. A heavily reinforced, short and wide implant 200 as measured on the outer surface of the porous body 206, is particularly suited for replacement of molars. Thus, in one example embodiment, the porous body 206 may provide outer dimensions of a width w of approximately 6 mm and a height h of approximately 6 mm. The reinforcing members 208 are disposed and oriented similarly to that of reinforcing members 178, 180, 182, and 184 in implant 170 mentioned above. In this embodiment, however, the reinforcing members 208 are not connected to the abutment connector 202 and do not angle inward.

It will be appreciated that other configurations for the reinforcing in FIGS. 11-13 may be provided than that shown including more or less reinforcing members. The reinforcing members may be provided in addition to a central core of a different material than the porous body or may be provided instead of such a central core. The reinforcing members may also generally extend in directions other than, or in addition to, a coronal-apical (or superior-inferior) direction.

From the foregoing, it will be understood that the reinforcing for the porous material may include a core, whether a central core, off-center, solid, or entirely or partially hollow. The reinforcing may additionally or alternatively include off-center reinforcement members, whether or not a central core is present, and the reinforcing may protrude through the porous material, whether or not the core also protrudes through the porous material.

The porous body 206, as well as any of the porous bodies and porous sleeves described herein, may have a tapered outer surface 212 similar to tapered surface 162.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dental implant, comprising:
    an elongated implant body having opposed coronal and apical ends;
    an abutment connector having correspondingly opposed coronal and apical ends, the abutment connector including a recess for receiving the coronal end of the body at the apical end of the abutment connector, the apical end of the abutment connector defining a non-threaded press-fit connection between the abutment connector and the coronal end of the body, the abutment connector being adapted for connection to an abutment at its coronal end, the abutment connector further defining a core extending from its coronal end to its apical end;
    both the implant body and abutment connector having correspondingly aligned bores configured for receiving a retaining screw;
    wherein the implant body further comprises a plurality of reinforcing members embedded within the body.

2. A dental implant, comprising:

an elongated implant body of porous tantalum having opposed coronal and apical ends, the body defining a longitudinal, central axis;

a plurality of reinforcing members extending within the body, the members being generally aligned with, but angled inwardly with respect to, the central axis of the body in a direction extending from the coronal to the apical end of the body, each of the plurality of reinforcing members being configured as an elongated bar, and at least one of the plurality of reinforcing members being spaced radially from the longitudinal, central axis by at least a portion of the porous tantalum of the body;

an abutment connector disposed on the coronal end of the body, the plurality of reinforcing members extending from the abutment connector;

wherein the dental implant further comprises a core made of a different material from the body and extending along the longitudinal, central axis and spaced from the plurality of reinforcing members.

3. The dental implant of claim 2, wherein the plurality of reinforcing members are generally uniformly spaced around the longitudinal, central axis.

4. The dental implant of claim 2, wherein the body has a varying cross-sectional dimension.

* * * * *